(12) United States Patent
Isaacson

(10) Patent No.: US 8,670,810 B2
(45) Date of Patent: Mar. 11, 2014

(54) REGIONAL OXIMETRY ANALOG FRONT END

(75) Inventor: Philip O. Isaacson, Chanhassen, MN (US)

(73) Assignee: Nonin Medical, Inc., Plymouth, MN (US)

( * ) Notice: Subject to any disclaimer, the term of this patent is extended or adjusted under 35 U.S.C. 154(b) by 258 days.

(21) Appl. No.: 12/794,420

(22) Filed: Jun. 4, 2010

(65) Prior Publication Data

US 2010/0312080 A1    Dec. 9, 2010

Related U.S. Application Data

(60) Provisional application No. 61/184,511, filed on Jun. 5, 2009.

(51) Int. Cl.
*A61B 5/05* (2006.01)

(52) U.S. Cl.
USPC .......................................................... 600/323

(58) Field of Classification Search
USPC .......................................................... 600/323
See application file for complete search history.

(56) References Cited

U.S. PATENT DOCUMENTS

| 4,267,844 A * | 5/1981 | Yamanishi ............... 600/315 |
| 6,181,959 B1 * | 1/2001 | Schollermann et al. ...... 600/323 |
| 2009/0163784 A1 * | 6/2009 | Sarpeshkar et al. .......... 600/322 |

OTHER PUBLICATIONS

Allen, D. H, et al., "Logarithmic Detector for Pulsed Lasers", *Applied Optics*, 11(2), (1972), 476-477.

* cited by examiner

*Primary Examiner* — Clayton E LaBalle
*Assistant Examiner* — Noam Reisner
(74) *Attorney, Agent, or Firm* — Schwegman, Lundberg & Woessner, P.A.

(57) ABSTRACT

An apparatus includes a first amplifier having a first input coupled to a first optical detector. The first amplifier includes a first output corresponding to a logarithm of the first input. The apparatus includes a second amplifier having a second input coupled to a second optical detector and having a second output corresponding to a logarithm of the second input. The apparatus includes a differential amplifier configured to amplify a difference between the first output and the second output.

29 Claims, 1 Drawing Sheet

REGIONAL OXIMETRY ANALOG FRONT END

CLAIM OF PRIORITY

This document claims the benefit of priority, under 35 U.S.C. Section 119(e), to Phillip O. Isaacson, U.S. Provisional Patent Application Ser. No. 61/184,511, entitled "REGIONAL OXIMETRY ANALOG FRONT END," filed on Jun. 5, 2009, which is incorporated herein by reference.

BACKGROUND

Technology for measuring oximetry is inadequate. Oximetry can be determined based on optical properties of tissue however systems for analyzing those properties do not provide satisfactory results.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Regional oximetry can determined by calculating a difference in optical absorbance along one or more pairs of paths from a particular light source. Absorbance is defined as the negative logarithm of the ratio of light intensity (or attenuation of light). Absorbance, also called optical density, can be determined using the natural logarithm or the common logarithm. Absorbance of a sample is proportional to the thickness of the sample as well as the concentration of absorbing species in the sample. According to one example, a photodetector can provide an electric current that is proportional to the light intensity.

Figure 1:
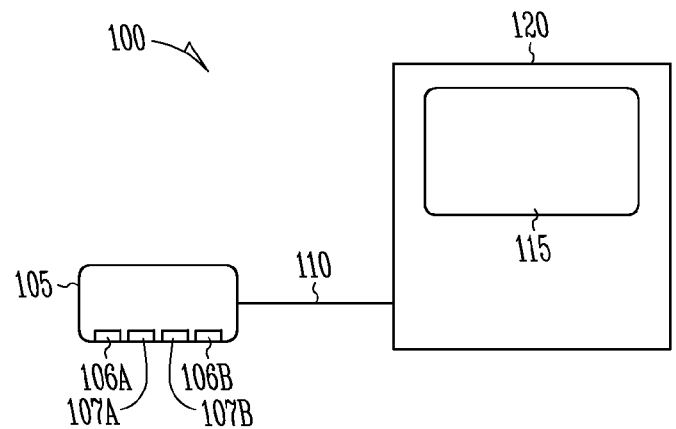
FIG. 1 illustrates a block diagram of an oximetry system according to one example.

FIG. 1 illustrates a block diagram of oximetry system 100 according to one example. System 100 includes sensor 105 coupled to device 120 by link 110.

In the example illustrated, sensor 105 is configured for optical detection of one or more tissue parameters. However, in other examples, sensor 105 can be configured for measuring a parameter using non-optical means such as, for example, thermal, pressure, and other detection means.

Sensor 105 includes optical detector 106A and optical detector 106B. Detectors 106A and 106B can include a photodetector responsive to light of a particular wavelength. Sensor 105 also includes emitter 107A and emitter 107B. The arrangement of emitters and detectors can be configured to provide a number of different tissue traversal paths. The paths can have differing depths of penetration within the tissue and be tailored for use at a particular wavelength of sensitivity.

Sensor 105 is coupled to device 120 by link 110. Link 110 can include a wired connection or a wireless coupling. In one example, link 110 includes a wired connection of approximately 18" length. In one example, link 110 can include a fiber optic element or a radio frequency (RF) communication link.

Device 120 includes circuitry to process the detected signal received from sensor 105. In the example shown, device 120 includes screen 115 configured to display visible data or configured as a touch-sensitive screen to receive a user input. Circuitry of device 120 can include any combination of analog circuitry and digital circuitry.

Figure 2:
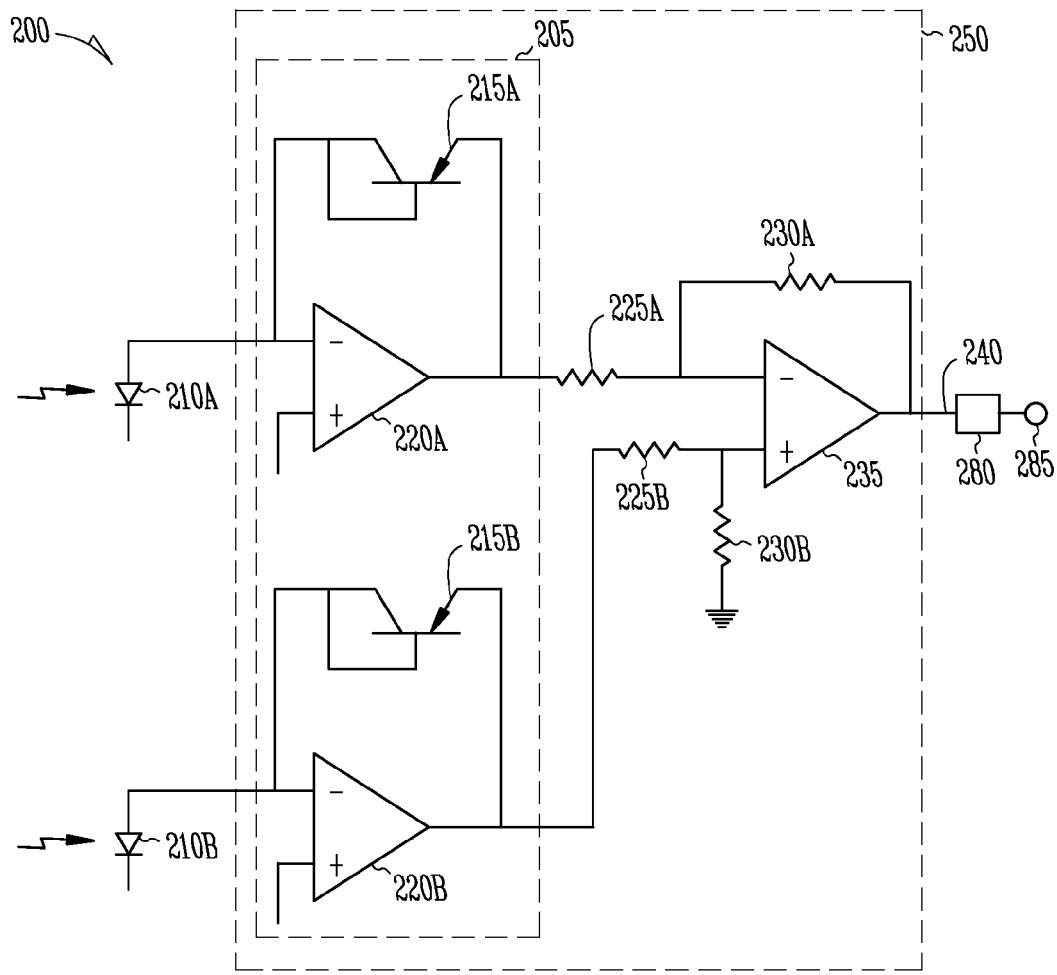
FIG. 2 illustrates an electrical schematic of an oximetry circuit according to one example.

In one example, device 120 includes an analog circuit such as that shown in FIG. 2.

FIG. 2 includes a front end circuit for receiving and processing a detected low level signal such as that provided by detectors 106A and 106B of FIG. 1.

In FIG. 2, apparatus 200 includes photodetectors 210A and 210B which, in one example, correspond with detectors 106A and 106B. Apparatus 200 also includes circuit 250 having a configuration of operational amplifiers and feedback elements. An output of circuit 250, at 240, is coupled to module 280. Module 280 has an output at node 285. In one example, detectors 106A and 106B are wirelessly coupled to device 120 and are modeled in FIG. 2 as photodetectors 210A and 210B. Apparatus 200 can include a housing. The housing can be configured for regional oximetry and can include structure to hold optical detectors in a particular configuration.

In the example shown, photodetectors 210A and 210B are sensitive to light of a particular wavelength. Outputs from photodetectors 210A and 210B are provided to an inverting terminal of amplifier 220A and amplifier 220B, respectively. In one example, amplifier 220A and amplifier 220B include an operational amplifier (op-amp).

Feedback from amplifier 220A is coupled to the inverting terminal via transistor 215A. In addition to a transistor, other non-linear elements can be used in the feedback loop. In a similar manner, feedback from amplifier 220B is coupled to the inverting terminal via transistor 215B. The combination of amplifier and non-linear feedback, as shown, provides a circuit that can be referred to as a logarithmic amplifier. The feedback path can include a transistor junction.

In the example shown, the dual logarithmic amplifiers are located within a common package denoted by dotted line 205. When operating, package 205 assures that a temperature of amplifier 220A is relatively close to the temperature of amplifier 220B. In one example, package 205 is fabricated using a semiconductor fabrication process that provides good uniformity of process, voltage and temperature (PVT) and thus, provides well matched performance.

The output signals of logarithmic amplifiers 220A and 220B are coupled to differential amplifier 235 via series input resistors 225A and 225B, respectively. Feedback derived from output 240 of amplifier 235 is coupled, by series resistor 230A, to the inverting terminal of amplifier 235. In addition, the non-inverting terminal of amplifier 235 is shunted to ground by resistor 230B. In this configuration, output 240 of amplifier 235 provides an amplified version of the difference signal derived from the logarithmic amplifiers 220A and 220B.

Apparatus 200 can be configured to provide a signal corresponding to a tissue characteristic. The tissue characteristic can be based on a parameter of blood in the tissue. For example, the parameter can include a chromophore. A chromophore is part of a molecule responsible for color. An example of a chromophore is hemoglobin. In one example, the tissue characteristic includes a measure of a hemoglobin index. The index can represent a ratio of quantity of tissue and quantity of blood. In addition, the tissue characteristic can represent a measure of regional oximetry.

Module 280 is coupled to circuit 250. Module 280 can include an analog circuit, a digital circuit or a combination of analog and digital circuit. For example, module 280 can include an anti-logarithm circuit, and as such, node 285 can be configured to provide a raw ratio of the light intensities as measured by photodetectors 210A and 210B. Module 280 can include an operational amplifier, a computational unit, a display, a memory, or other circuit.

The difference in absorbance, as determined using different optical paths, can be used to provide a measure of regional oximetry. In particular, absorbance is proportional to the logarithm of the light intensity. In addition, the light intensity is proportional to the current provided by the photodetectors at the front end.

To determine absorbance, one example of the present subject matter uses a pair of logarithmic current-to-voltage amplifiers coupled to a difference amplifier.

In one example shown herein, two pairs of light emitters and two pairs of photodetectors are used. The calculation to determine oximetry entails determining the sum of the absorbance along two longer paths minus the absorbance along two shorter paths through the tissue.

A sample and hold circuit can be used to determine oximetry. An output from the sample-and-hold circuit can be coupled to a difference amplifier or the signal can be digitized and a processor can be used to determine a difference. The difference cancels out any offsets in the logarithmic amplifiers.

The results following the second difference are independent of the offsets of the amplifiers, however, the logarithmic gains will vary with the temperature of the silicon transistors used as logarithmic (non-linear) elements. As such, matched transistors in a common package can be used to mitigate the effects of temperature variation.

In one example, regional oximetry uses two or more wavelengths strobed sequentially. As shown in the figure, photodetectors 210A and 210B provide a signal corresponding to the optical wavelengths.

The logarithmic amplifiers can be configured to use ambient current removal.

The present subject matter can be used for regional oximetry or other applications utilizing the difference in absorbance along two paths.

In one example, a first path provides a reference path and the second path provides a measurement path.

An example of the present subject matter can be configured for determining a ratio of detected light. As such, an anti-logarithmic element can be coupled to the output in order to determine a raw ratio. The anti-logarithmic element can include an operational amplifier or a computational element (analog or digital).

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    a first amplifier having a first input coupled to a first optical detector and having a first output corresponding to a logarithm of the first input wherein the first input corresponds to light intensity along a first optical path through a tissue, the first optical detector on the first optical path;
    a second amplifier having a second input coupled to a second optical detector and having a second output corresponding to a logarithm of the second input wherein the second input corresponds to light intensity along a second optical path through the tissue, the second optical detector on the second optical path and wherein the first optical path differs from the second optical path, wherein the light intensity corresponds to concentration of an absorbing species in the tissue; and
    a differential amplifier having a differential output, the differential amplifier configured to amplify a difference between the first output and the second output and generate an output signal, the output signal provided at the differential output and the output signal corresponding to oxygenation of a region of the tissue.

2. The apparatus of claim 1 wherein the first optical detector is coupled to an inverting input of the first amplifier.

3. The apparatus of claim 1 wherein the second optical detector is coupled to an inverting input of the second amplifier.

4. The apparatus of claim 1 wherein at least one of the first amplifier and the second amplifier includes an operational amplifier.

5. The apparatus of claim 1 wherein at least one of the first amplifier and the second amplifier includes a feedback path having a transistor junction.

6. The apparatus of claim 1 wherein the first optical detector and the second optical detector are responsive to light intensity.

7. The apparatus of claim 1 wherein the first optical detector and the second optical detector are configured to provide a signal corresponding to light absorbance.

8. The apparatus of claim 1 wherein the first amplifier matches the second amplifier.

9. The apparatus of claim 1 wherein the first amplifier and the second amplifier are in a common package.

10. The apparatus of claim 1 wherein the differential output is coupled to a module, the module configured to determine a measure of a tissue characteristic.

11. The apparatus of claim 10 wherein the module is configured to determine a characteristic of blood in the tissue.

12. The apparatus of claim 10 wherein the module is configured to determine a measure of a chromophore.

13. The apparatus of claim 10 wherein the module is configured to determine a measure of hemoglobin.

14. The apparatus of claim 10 wherein the module is configured to determine a hemoglobin index corresponding to a ratio of tissue and blood.

15. The apparatus of claim 10 wherein the module includes a display.

16. A method comprising:
receiving a first signal from a first optical detector, the first signal corresponding to a first optical parameter for a tissue wherein the first optical parameter corresponds to light intensity along a first optical path through the tissue;
receiving a second signal from a second optical detector, the second signal corresponding to a second optical parameter for the tissue wherein the second optical parameter corresponds to light intensity along a second optical path through the tissue, wherein the first optical path differs from the second optical path, wherein the light intensity corresponds to concentration of an absorbing species in the tissue;
generating a first amplified output corresponding to a logarithm of the first signal;
generating a second amplified output corresponding to a logarithm of the second signal; and
generating a differential output using the first amplified output and the second amplified output, wherein the differential output corresponds to oxygenation of a region of the tissue.

17. The method of claim 16 wherein at least one of receiving the first signal or receiving the second signal includes receiving a measure of light absorbance.

18. The method of claim 16 wherein generating the first amplified output includes providing the first signal to an inverting input of an operational amplifier.

19. The method of claim 16 wherein generating the second amplified output includes providing the second signal to an inverting input of an operational amplifier.

20. The method of claim 16 wherein generating the first amplified output and generating the second amplified output includes providing the first signal and the second signal to a common package.

21. The method of claim 16 further including using the differential output to determine a measure of oximetry.

22. The method of claim 21 further including displaying the measure.

23. A system comprising:
a first optical detector configured to provide a first signal corresponding to a first optical property of a tissue wherein the first optical property corresponds to light intensity along a first optical path through the tissue;
a second optical detector configured to provide a second signal corresponding to a second optical property of the tissue wherein the second optical property corresponds to light intensity along a second optical path through the tissue, wherein the first optical path differs from the second optical path, wherein the light intensity corresponds to concentration of an absorbing species in the tissue;
a first amplifier to generate a first output corresponding to a logarithm of the first signal;
a second amplifier to generate a second output corresponding to a logarithm of the second signal;
a differential amplifier configured to generate a differential output corresponding to oxygenation of a region of the tissue and based on the first output and the second output; and
a display configured to provide a visible indication corresponding to the differential output.

24. The system of claim 23 wherein the first optical detector and the second optical detector are coupled to a sensor housing.

25. The system of claim 24 wherein the sensor housing is configured for regional oximetry.

26. The system of claim 23 wherein the first amplifier and the second amplifier are configured as a single package.

27. The system of claim 23 wherein at least one of the first amplifier and the second amplifier includes a feedback path having a transistor junction.

28. The system of claim 23 wherein the first amplifier matches the second amplifier.

29. The system of claim 23 wherein the visible indication corresponds to a measure of regional oximetry.

* * * * *